US009572943B2

(12) United States Patent
Giroux

(10) Patent No.: US 9,572,943 B2
(45) Date of Patent: *Feb. 21, 2017

(54) PARTICLE DISPERSION DEVICE FOR NASAL DELIVERY

(71) Applicant: Kurve Technology, Inc., Lynnwood, WA (US)

(72) Inventor: Marc Giroux, Lynnwood, WA (US)

(73) Assignee: Kurve Technology, Inc., Lynnwood, WA (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/901,415

(22) Filed: May 23, 2013

(65) Prior Publication Data

US 2013/0263846 A1 Oct. 10, 2013

Related U.S. Application Data

(63) Continuation of application No. 12/960,311, filed on Dec. 3, 2010, now Pat. No. 8,448,637, which is a continuation of application No. 11/522,495, filed on Sep. 14, 2006, now Pat. No. 7,866,316, which is a continuation of application No. 10/262,430, filed on Sep. 30, 2002, now Pat. No. 7,231,919.

(60) Provisional application No. 60/379,428, filed on May 9, 2002, provisional application No. 60/325,971, filed on Sep. 28, 2001.

(51) Int. Cl.

| | |
|---|---|
| *A61M 11/00* | (2006.01) |
| *A61M 15/00* | (2006.01) |
| *A61M 16/06* | (2006.01) |
| *A61M 15/08* | (2006.01) |

(52) U.S. Cl.

CPC ........... *A61M 11/00* (2013.01); *A61M 11/001* (2014.02); *A61M 15/0008* (2014.02); *A61M 15/0028* (2013.01); *A61M 15/0086* (2013.01); *A61M 15/08* (2013.01); *A61M 16/06* (2013.01); *A61M 2206/16* (2013.01); *A61M 2210/0618* (2013.01)

(58) Field of Classification Search

CPC A61M 15/009; A61M 15/0086; A61M 15/08; A61M 15/085; A61M 11/00; A61M 15/0028; A61M 16/06; A61M 2206/16; A61M 2210/0618; A61M 11/001; A61M 15/0008

USPC .......................... 128/203.15, 203.12, 207.13

See application file for complete search history.

(56) References Cited

U.S. PATENT DOCUMENTS

| | | | |
|---|---|---|---|
| 2,503,732 | A | 4/1950 | Heisterkamp |
| 2,603,216 | A | 7/1952 | Taplin |
| 2,819,716 | A | 1/1958 | Miller |
| 2,951,644 | A | 9/1960 | Mahon |

(Continued)

FOREIGN PATENT DOCUMENTS

| | | | |
|---|---|---|---|
| EP | 0539674 | B1 | 5/1993 |
| EP | 0734719 | A1 | 10/1996 |

(Continued)

OTHER PUBLICATIONS

Hess, D. et al., "Medication Nebulizer Performance: Effects of Diluent Volume, Nebulizer Flow, and Nebulizer Brand," Chest 110(2):498-505, Aug. 1996.

(Continued)

*Primary Examiner* — Steven Douglas

(57) ABSTRACT

A nebulizer and a method of breathing using the nebulizer is described. The nebulizer and breathing techniques are capable of delivering medicament into the sinus cavity of a user.

22 Claims, 12 Drawing Sheets

(56) References Cited

U.S. PATENT DOCUMENTS

| | | |
|---|---|---|
| 3,155,573 A | 11/1964 | Fowler |
| 3,358,844 A | 12/1967 | Klein |
| 3,362,405 A | 1/1968 | Hazel |
| 3,379,381 A | 4/1968 | Decaux |
| 3,762,409 A | 10/1973 | Lester |
| 3,858,615 A | 1/1975 | Weigl |
| 3,973,566 A | 8/1976 | Mathes |
| 4,069,819 A | 1/1978 | Valentini |
| 4,119,096 A | 10/1978 | Drews |
| 4,150,071 A | 4/1979 | Pecina |
| 4,157,368 A | 6/1979 | Fernandes |
| 4,198,969 A | 4/1980 | Virag |
| 4,241,877 A | 12/1980 | Hughes |
| 4,299,784 A | 11/1981 | Hense |
| 4,453,542 A | 6/1984 | Hughes |
| 4,454,880 A | 6/1984 | Muto |
| 4,461,425 A | 7/1984 | Miller |
| 4,554,916 A | 11/1985 | Watt |
| 4,690,332 A | 9/1987 | Hughes |
| 4,702,415 A | 10/1987 | Hughes |
| 4,750,650 A | 6/1988 | Ling |
| 4,801,093 A | 1/1989 | Brunet |
| 4,809,692 A | 3/1989 | Nowacki |
| 4,809,706 A | 3/1989 | Watson |
| 4,865,027 A | 9/1989 | Laanen |
| 4,938,209 A | 7/1990 | Fry |
| 4,953,545 A | 9/1990 | McCarty |
| 4,972,830 A | 11/1990 | Wong |
| 5,033,463 A | 7/1991 | Cocozza |
| 5,063,922 A | 11/1991 | Häkkinen |
| 5,064,122 A | 11/1991 | Kamishita |
| 5,067,655 A | 11/1991 | Farago |
| 5,096,467 A | 3/1992 | Matsui |
| 5,201,726 A | 4/1993 | Kirkham |
| 5,203,323 A | 4/1993 | Tritle |
| 5,207,217 A | 5/1993 | Cocozza |
| 5,241,954 A | 9/1993 | Glenn |
| 5,287,847 A | 2/1994 | Piper |
| 5,301,663 A | 4/1994 | Small, Jr. |
| 5,309,900 A | 5/1994 | Knoch |
| 5,322,057 A | 6/1994 | Raabe |
| 5,322,646 A | 6/1994 | Wright |
| 5,331,953 A | 7/1994 | Andersson |
| 5,347,998 A | 9/1994 | Hodson |
| 5,349,947 A | 9/1994 | Newhouse |
| 5,388,574 A | 2/1995 | Ingebrethsen |
| 5,392,767 A | 2/1995 | Bianco |
| 5,427,089 A | 6/1995 | Kraemer |
| 5,435,282 A | 7/1995 | Haber |
| 5,437,267 A | 8/1995 | Weinstein |
| 5,458,135 A | 10/1995 | Patton |
| 5,476,093 A | 12/1995 | Lankinen |
| 5,479,920 A | 1/1996 | Piper |
| 5,485,828 A | 1/1996 | Hauser |
| 5,487,378 A | 1/1996 | Robertson |
| 5,490,630 A | 2/1996 | Hecker |
| 5,497,765 A | 3/1996 | Praud |
| 5,497,944 A | 3/1996 | Weston |
| 5,505,193 A | 4/1996 | Ballini |
| 5,520,167 A | 5/1996 | Hamilton |
| 5,522,383 A | 6/1996 | Calvert |
| 5,577,497 A | 11/1996 | Mecikalski |
| 5,584,285 A | 12/1996 | Salter |
| 5,586,551 A | 12/1996 | Hilliard |
| 5,588,564 A | 12/1996 | Hutson |
| 5,685,291 A | 11/1997 | Marsh |
| 5,687,710 A | 11/1997 | Ambrosio |
| 5,687,912 A | 11/1997 | Denyer |
| 5,711,488 A | 1/1998 | Lund |
| 5,724,965 A | 3/1998 | Handke |
| 5,743,250 A | 4/1998 | Gonda |
| 5,755,218 A | 5/1998 | Johansson |
| 5,775,320 A | 7/1998 | Patton |
| 5,785,049 A | 7/1998 | Smith |
| 5,819,730 A | 10/1998 | Stone |
| 5,855,202 A | 1/1999 | Andrade |
| 5,860,416 A | 1/1999 | Howlett |
| 5,875,774 A | 3/1999 | Clementi |
| 5,881,720 A | 3/1999 | Vinogradov |
| 5,906,198 A | 5/1999 | Flickinger |
| 5,950,623 A | 9/1999 | Michell |
| 5,954,049 A | 9/1999 | Foley |
| 5,997,848 A | 12/1999 | Patton |
| 6,062,214 A | 5/2000 | Howlett |
| 6,073,629 A | 6/2000 | Hardy |
| 6,076,520 A | 6/2000 | Cooper |
| 6,085,740 A | 7/2000 | Ivri |
| 6,095,141 A | 8/2000 | Armer |
| 6,112,746 A | 9/2000 | Kwok |
| 6,119,694 A | 9/2000 | Correa |
| 6,131,568 A | 10/2000 | Denyer |
| 6,138,668 A | 10/2000 | Patton |
| 6,158,428 A | 12/2000 | Mecikalski |
| 6,192,876 B1 | 2/2001 | Denyer |
| 6,202,643 B1 | 3/2001 | Sladek |
| 6,223,744 B1 | 5/2001 | Garon |
| 6,234,459 B1 | 5/2001 | Rock |
| 6,240,917 B1 | 6/2001 | Andrade |
| 6,244,573 B1 | 6/2001 | Rock |
| 6,269,810 B1 | 8/2001 | Brooker |
| 6,302,101 B1 | 10/2001 | Py |
| 6,338,443 B1 | 1/2002 | Piper |
| 6,347,629 B1 | 2/2002 | Braithwaite |
| 6,367,471 B1 | 4/2002 | Genosar |
| 6,394,085 B1 | 5/2002 | Hardy |
| 6,412,488 B1 | 7/2002 | Barnett |
| 6,418,925 B1 | 7/2002 | Genova |
| 6,468,330 B1 | 10/2002 | Irving |
| 6,470,882 B1 | 10/2002 | Newhouse |
| 6,543,448 B1 | 4/2003 | Smith |
| 6,550,472 B2 | 4/2003 | Litherland |
| 6,575,160 B1 | 6/2003 | Volgyesi |
| 6,576,224 B1 | 6/2003 | Osbakken |
| 6,595,210 B2 | 7/2003 | Ohki |
| 6,651,655 B1 | 11/2003 | Licalsi |
| 6,702,997 B2 | 3/2004 | Chaudry |
| 6,705,316 B2 | 3/2004 | Blythe |
| 6,715,485 B1 | 4/2004 | Djupesland |
| 6,749,597 B2 | 6/2004 | Frank |
| 6,796,513 B2 | 9/2004 | Fraccaroli |
| 6,805,118 B2 | 10/2004 | Brooker |
| 6,810,872 B1 | 11/2004 | Ohki |
| RE38,700 E | 2/2005 | Briggs, III |
| 6,851,626 B2 | 2/2005 | Patel |
| 6,883,517 B2 | 4/2005 | Halamish |
| 6,948,491 B2 | 9/2005 | Loeffler |
| 6,994,083 B2 | 2/2006 | Foley |
| 7,231,919 B2 | 6/2007 | Giroux |
| 7,866,316 B2 | 1/2011 | Giroux |
| 8,122,881 B2 | 2/2012 | Giroux |
| 2001/0029947 A1 | 10/2001 | Paboojian |
| 2002/0033173 A1 | 3/2002 | Shofner, II |
| 2002/0073997 A1 | 6/2002 | Keane |
| 2002/0088463 A1 | 7/2002 | Keane |
| 2002/0089072 A1 | 7/2002 | Rock |
| 2002/0124843 A1 | 9/2002 | Skiba |
| 2003/0078551 A1 | 4/2003 | Hochrainer |
| 2003/0079742 A1 | 5/2003 | Giroux |
| 2003/0150452 A1 | 8/2003 | Staniforth |
| 2004/0025871 A1 | 2/2004 | Davies |
| 2004/0112379 A1 | 6/2004 | Djupesland |
| 2004/0164099 A1 | 8/2004 | Diestelhorst |

FOREIGN PATENT DOCUMENTS

| | | |
|---|---|---|
| EP | 0747078 B1 | 12/1996 |
| GB | 1069048 A | 5/1967 |
| JP | 8280809 A | 10/1996 |
| WO | 93/01891 A1 | 2/1993 |
| WO | 98/26827 A1 | 6/1998 |
| WO | 98/41256 A2 | 9/1998 |
| WO | 99/47273 A2 | 9/1999 |
| WO | 01/02024 A1 | 1/2001 |
| WO | 01/36033 A2 | 5/2001 |

(56) References Cited

FOREIGN PATENT DOCUMENTS

| WO | 01/43794 A2 | 6/2001 |
|----|-------------|--------|
| WO | 01/49350 A1 | 7/2001 |
| WO | 03/026559 A2 | 4/2003 |
| WO | 2005/023335 A2 | 3/2005 |

OTHER PUBLICATIONS

Hess, D.R., "Nebulizers: Principles and Performance," Respiratory Care 45(6):609-622, 2000.
Loffert, D.T., et al., "A Comparison of Commercial Jet Nebulizers," Chest 106(6):1788-1792, Dec. 1994.
O'Callaghan, C., and P.W. Barry, "The Science of Nebulised Drug Delivery," Thorax 52(Suppl 2):S31-S44, 1997.
Zhao, K., et al., "Effect of Anatomy of Human Nasal Air Flow and Odorant Transport Patterns: Implications for Olfaction," Chemical Senses 29(5):365-379, 2004.
Giroux, M., "Nasal Nebulizer," U.S. Appl. No. 60/325,971, filed Sep. 28, 2001.
Giroux, M., "Nasal Nebulizer," U.S. Appl. No. 60/379,428, filed May 9, 2002.
European Search Report mailed Jan. 19, 2005, in European Patent Application No. 02778422.2, filed Sep. 30, 2002, 10 pages.
International Search Report mailed Apr. 1, 2003, in International Patent Application No. PCT/US2002/031450, 2 pages.
International Search Report mailed Oct. 16, 2003, in International Patent Application No. PCT/US2003/014786, 2 pages.

PARTICLE DISPERSION DEVICE FOR NASAL DELIVERY

CROSS-REFERENCE(S) TO RELATED APPLICATION(S)

This application is a continuation of U.S. patent application Ser. No. 12/960,311, filed Dec. 3, 2010 and entitled PARTICLE DISPERSION DEVICE FOR NASAL DELIVERY (now U.S. Pat. No. 8,448,637, issued on May 28, 2013), which is a continuation of U.S. patent application Ser. No. 11/522,495, filed Sep. 14, 2006, and entitled PARTICLE DISPERSION DEVICE FOR NASAL DELIVERY (now U.S. Pat. No. 7,866,316, issued on Jan. 11, 2011), which is a continuation of U.S. patent application Ser. No. 10/262,430, filed Sep. 30, 2002, and entitled PARTICLE DISPERSION DEVICE FOR NASAL DELIVERY (now U.S. Pat. No. 7,231,919, issued on Jun. 19, 2007), which claims the benefit of priority to U.S. Provisional Application No. 60/379,428, filed May 9, 2002, and entitled NASAL NEBULIZER and 60/325,971, filed Sep. 28, 2001, and entitled NASAL NEBULIZER, all of which are incorporated by reference herein in their entirety.

FIELD OF THE INVENTION

This invention relates to devices for administration of therapeutic agents to the nasal cavity and paranasal sinuses of a patient.

BACKGROUND

In the United States, sixty million people suffer from chronic sinusitis and allergic rhinitis and are treated by means of antihistamines, antibiotics, decongestants, and pain relievers. Many of these drugs would work more effectively in relieving symptoms if they could be directly applied to all of the affected areas. However, the devices utilized thus far to deliver these drugs have proven to be extremely inadequate, if not useless, in reaching all areas needed especially the deep nasal cavity and paranasal sinuses where it is critical in the treatment of some of these diseases. There is a need for a more effective device to administer these medicines to all the areas of the nasal cavity and paranasal sinuses.

A current delivery system consists of a pressurized canister (MDI) that ejects the medicine into the nostrils in short bursts, or streams of atomized liquid in an aqueous nasal spray. The efficacy of medicine administered in this manner is limited due to difficulties in the medicine reaching very little of the nasal mucosa and no part of paranasal sinuses where it needs to be delivered to fully treat the condition. In cases of severe congestion or nasal polyps, the medicine often does not proceed beyond the nostril and will not be effectively absorbed into the bloodstream or the necessary area of the nasal cavity and paranasal sinuses. Current systems also do not allow particle sizes to be small enough to reach high into the nasal cavity and paranasal sinuses. There is a need for delivery system alternatives to better deliver more of the medicine to the nasal cavity and paranasal sinuses and of the sufferers of these diseases, and others.

A nebulizer is, for example, a machine that converts medicine into a mist, or vapor, of very tiny particles to deliver a drug to the lungs during an attack by breathing the medicine from a pipe attachment or, in the case of young children, a face mask. The particle size is important in that it allows passage of the drug through heavily congested airways over a period of about 10 minutes which allows for deep penetration. Nebulizers are used by asthmatics in case of an asthma attack.

Nasal nebulizers are currently in use for antibiotics and are ineffectively delivered due to the fact they do not deliver into the paranasal sinuses nor as far into the nasal cavity as this device due to the lack of additional technology enclosed herein.

SUMMARY OF THE INVENTION

A nebulizer and a method of breathing using the nebulizer is shown and described.

In a first embodiment, a controlled particle dispersion breathing method performed by a user having a sinus includes providing a nebulizer having a particle dispersion chamber to a user, the particle dispersion chamber capable of producing nebulized particles; activating the nebulizer; breathing a plurality of quick breaths as nebulized particles begin to flow out of the particle dispersion chamber; holding the quick breaths for a plurality of seconds; creating a pressure in the sinus of the user using the back of the throat; repeating the breathing a plurality of quick breaths, holding the quick breaths and creating a pressure in the sinuses; breathing a plurality of long breaths; and repeating the breathing a plurality of quick breaths, holding the quick breaths, creating a pressure in the sinuses and breathing a plurality of long breaths.

In another embodiment, a nebulizer is shown and described including a nasal adapter; a vortex chamber in communication with the nasal adapter; an outflow tube in communication with the dispersion chamber capable of causing a plurality of nebulized particles to move in a vortex within the internal channel of the nebulizer; and a housing, the housing having a medicine chamber in communication with the outflow tube.

In yet another embodiment, a particle dispersion chamber is shown and described including a housing having an external surface and an internal channel; and a plurality of air outputs communicating with the internal chamber, whereby the air outputs are capable of causing a plurality of nebulized particles to move in a vortex within the internal channel.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIG. 1 is a top planar view of one embodiment of the nasal nebulizer;

FIG. 2 is a frontal elevational view of the nasal nebulizer;

FIG. 3 is a side elevational view of the nasal nebulizer;

FIG. 4 is a bottom planar view of the nasal nebulizer;

FIG. 5 is a side cross-sectional view of the nasal nebulizer of FIG. 1 along line A-A showing internal components thereof;

FIG. 6 is a front view of one embodiment of the nasal adapter;

FIG. 7 is a rear view of the nasal adapter;

FIG. 8 is a side view of the tubing and nasal adapter;

FIG. 9 is a side view of another embodiment of the nebulizer showing the cartridge chamber;

DETAILED DESCRIPTION OF THE PREFERRED EMBODIMENT

Figure 1:
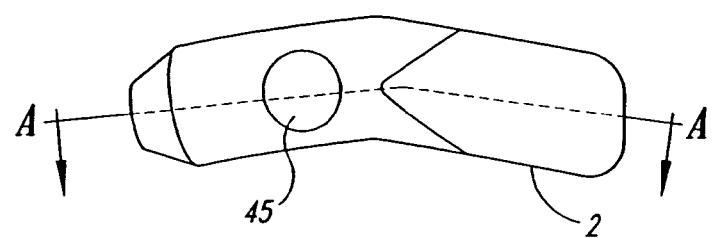

Current drug delivery methods are ineffective at penetrating very far into the nasal cavity and not at all into the paranasal sinuses. The nebulizer 25 has the ability to deliver the same drugs presently prescribed for diseases as very tiny particle doses of medicine via a nasal adapter 10 that allows more efficacious sinus penetration for the user. The particle sizes, time of application and particle dispersion technology allows the medicine to permeate the nasal cavity and most of the paranasal sinuses. All medicines currently applied by direct action to the nasal cavity and paranasal sinuses could be adapted for use with the nebulizer 25, and that would include over-the-counter nasal medicines for allergy and colds and flu.

For the user with the secondary condition of nasal polyps, this allows far more effective application of the medicine, which is often blocked by the polyp from penetrating even as much as the contemporary systems can. Corticosteroid-based inhalers are designed to also slow the re-growth of these polyps following their removal. Currently, they are largely ineffective at accomplishing this, often not being able to slow the growth at all. The apparatus and method described herein will be significantly more effective in slowing the re-growth of the polyps following their removal.

Many of the side effects of some medicines are eradicated by this method. With many sprays, the propellant causes a drying of the nasal passages leading to bleeds. With the use contemporary devices that lead to bleeds, a secondary spray of saline is added to the treatment in order to try and control the bleeding. Further, steroids in pill form have many unpleasant side effects such as internal bleeding, a redistribution of fluid to the head, neck and back causing unsightly "humps," and easy bruising, to name a few. An effective use of the nebulizer 25 does not have these side effects associated with steroids in pill form.

The nebulizer 25 will allow medicine to be administered to the nasal cavity and paranasal sinuses via very small particles that will penetrate deeply into the nasal cavity and most regions of the paranasal sinuses. It will also expose the patient to a more effective absorption of the drug, increasing effectiveness, and will allow multiple conditions to be treated in a far more effective manner. Since the medicine is delivered in a treatment and not an attack scenario, the application or delivery time is only 2-3 minutes rather than the 10-15 minutes used during an asthma attack. Multiple dose levels of the medicine will be placed in the nebulizer 25, a week supply for example, and the unit will run for a prescribed time, for example but not limited to three minutes, and will then shut itself off. The machine will be designed with multiple dose capability and a timer 4 with a pause feature 5. The pause feature 5 allows the user to stop the treatment under way to deal with a short, minor happenstance and then resume the treatment for the remaining time. The timer 4 will be variable to accommodate the drug being administered and/or prescribed by the physician.

The nebulizer 25 is capable of delivering particle sizes ranging from 2-50 microns, and in another aspect, from 2-15 microns, in order to keep the medicine inside the nasal cavity and the sinus chambers and prevent too much from passing through the chambers and into the lungs.

Figure 6:
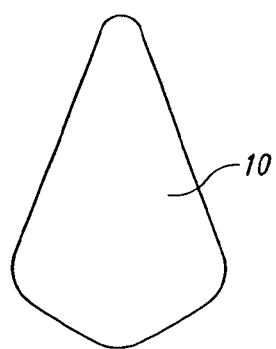
Figure 7:
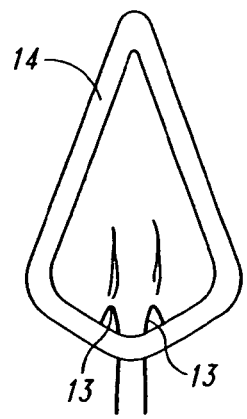
Figure 8:
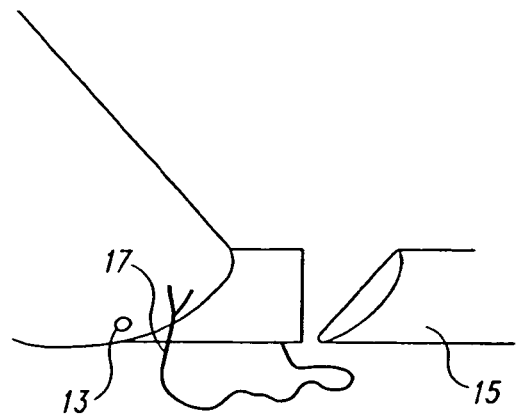

Referring now to the accompanying drawings, as shown in FIGS. 6-8, a nasal adapter 10 has been designed to attach to the outflow tube 15 of the nebulizer 25 to allow it to fit over the nasal openings and the nose itself restricting the flow of medicine to the nose alone. The nasal adapter 10 limits various unwanted occurrences such as delivery of any medicament to the eyes and face surrounding the nose and into the general environment.

Use of a nasal adaptor 10 also limits the spread and growth of bacteria or microorganisms. Use of a nasal adaptor 10 that fits over the nasal openings reduces the spread of bacteria that can be picked up from inside the nasal openings into or onto the delivery device if the nasal adaptor 10 were placed inside the nasal openings as is the case with current MDI's or AQ sprays. Further, use of a disposable nasal adaptor 10 that fits over the nasal openings reduces the occurrence of re-inoculation of the nasal openings with bacteria present on a nasal adaptor 10, when not properly cleaned, is reinserted into the nasal openings. Also, use of a disposable nasal adaptor 10 that fits over the nose reduces the extent of bacteria or microorganisms picked up from inside the nasal openings which can grow in the any tubing 80 associated with the nebulizer 25.

As shown in FIG. 7, the nasal adapter 10 has been designed with a lip 14 of material to seal the area around the nose keeping the aerosolized medicine away from the eyes and restricting the flow to the nasal passages. In one aspect of this embodiment, the nasal adapter 10 is approximately 1½ inches wide across the bridge of the nose and 1½ inches long. Other dimensions for the bridge width and length are envisioned. Further, in one aspect of the lip 14, the lip 14 on the nasal adapter 10 is approximately ⅛ inch long and is capable of forming a seal between the nasal adapter 10 and the face surrounding the nose. Other lip 14 widths are envisioned. In one aspect of this embodiment, the outflow tube 15 has an internal diameter of 9/16 of an inch and is tapered to fit or cooperate with the hose 9. Other diameters of the outflow tube 15 are envisioned and the device is not to be restricted to the above-mentioned diameter. As shown in FIG. 8, in one aspect, the nasal adapter 10 has been designed with exhaust valves or vent holes 13 on either side below the curve of the nose allowing necessary venting while keeping the aerosolized medicine away from the eyes.

Figure 2:
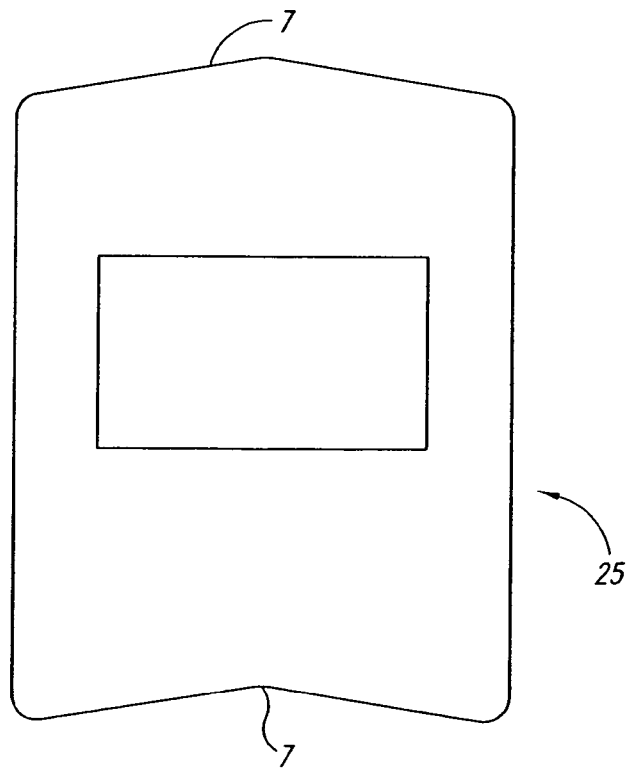
Figure 5:
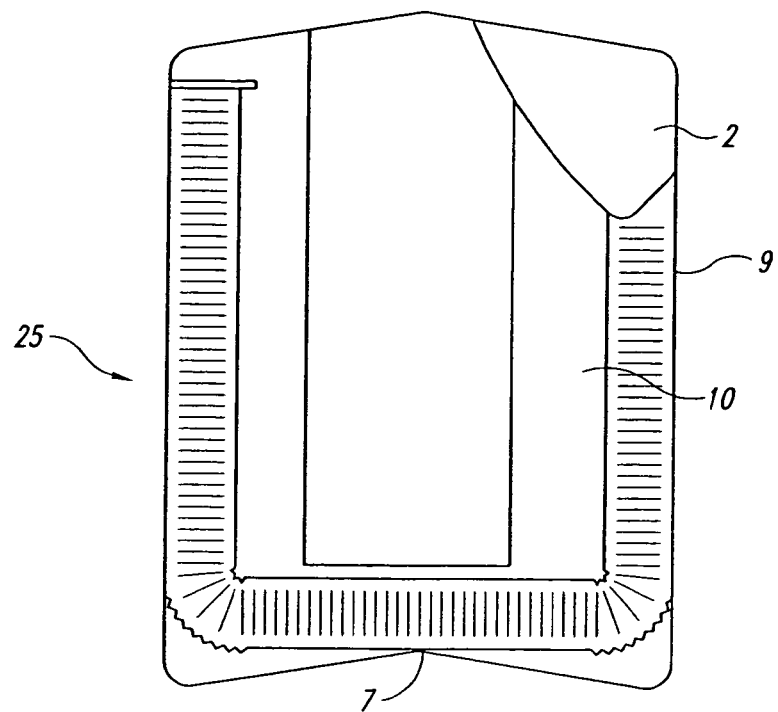

The nebulizer 25 has been greatly improved by being designed to accommodate daily use rather than occasional use as originally intended. As shown in FIG. 2, in one embodiment, it has been designed thinner and shorter with a hip-hugging curve 7 when in use in hands-free position. As shown in FIG. 8, for hands-free operation, the nasal adapter is equipped with elastic bands 17 that go around the head to hold the adapter in place while the treatment is delivered. As shown in FIG. 5, the nasal adapter can be attached to a hose 9 built into the device that can extend the reach to a standing person or a sitting person. In one aspect, the hose 9 is an accordion hose. In another embodiment, it can also be operated with the nasal adapter 10 attached directly to the unit outflow and held by hand to the nose for the duration of the treatment.

Figure 3:
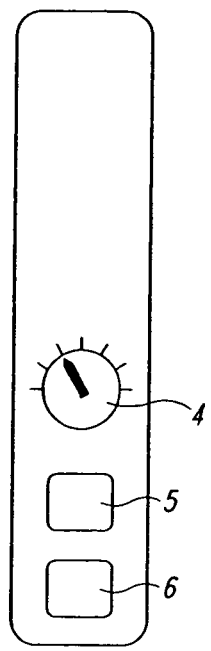
Figure 4:
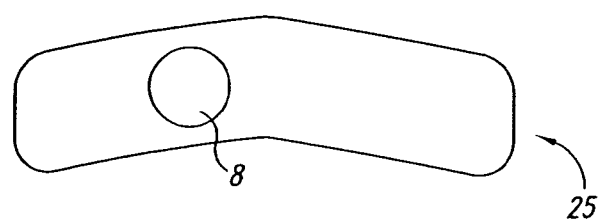
Figure 10:
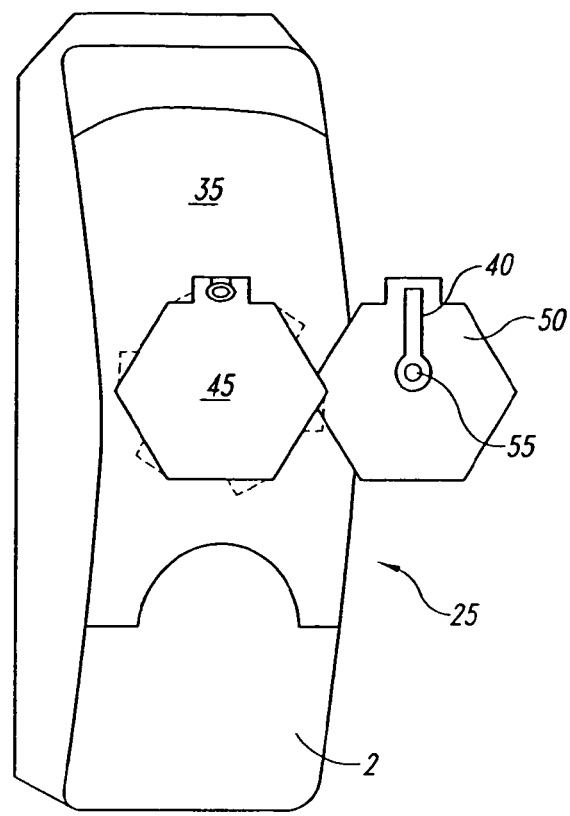
FIG. 10 is a top view of the nebulizer showing the cartridge chamber.

As shown in FIG. 4, an additional feature will be the multiple dose compartment 8 arrangement in which multiple doses of a medicament or compound may be placed inside the nebulizer 25. For example, in the case of chronic sinusitis, a week's worth of medicine will be placed into the nebulizer 25. As shown in FIG. 3, the nebulizer 25 has been designed with a timer 4 so that it will run for a programmed period of time and then turn itself off. As shown in FIG. 3, a pause feature 5 has been added to allow for dealing with minor disturbances and then resuming the treatment. The time allotted will depend upon the optimum time needed for the drug being dispensed and it has been designed to prevent evaporation for the duration of the predetermined supply. As shown in FIG. 10, the device can also be used in a single-dose application.

Figure 9:
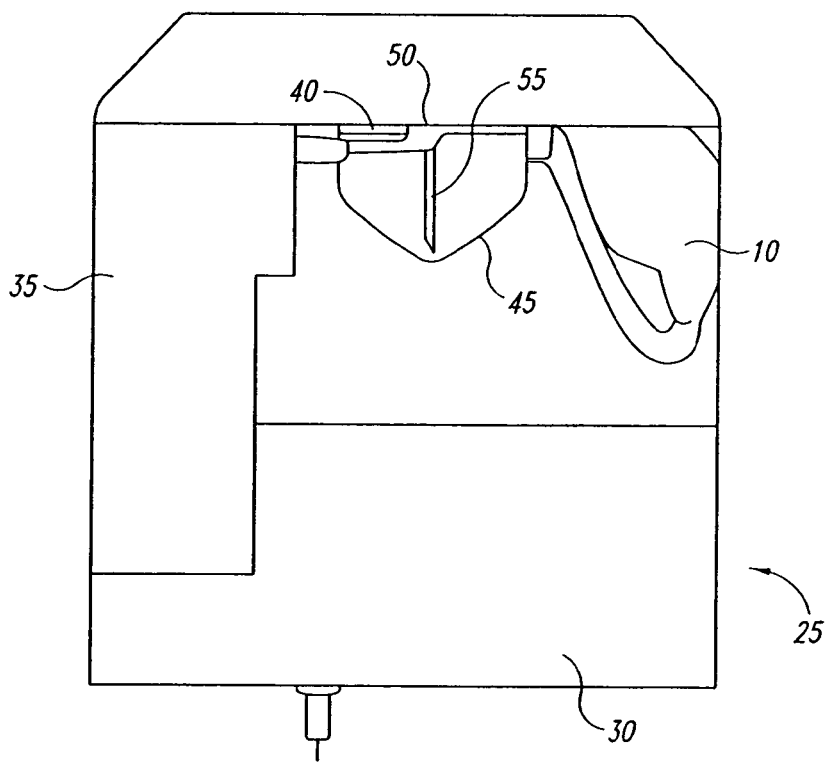

FIGS. 9 and 10 show one embodiment of the nebulizer 25. The nebulizer 25 may have a variety of dimensions but in one aspect, the nebulizer 25 is approximately three inches wide and approximately four inches high. The nebulizer 25 will generally include a power supply 30, a pump 35, a pump connector 40, a medicine chamber 45, a lid 50 for covering the medicine chamber and a nebulizing stem 55 for introduction into a cartridge 60 inserted into the medicine chamber 45. A nasal adapter 10 of varying sizes is associable with the nebulizer 25.

Figure 23:
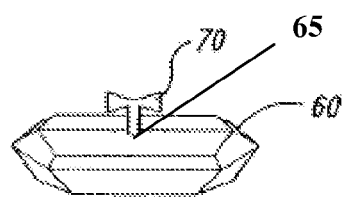
FIG. 23 shows a side view of one embodiment of the cartridge.
Figure 24:
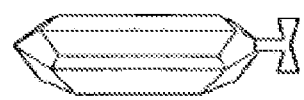
FIG. 24 shows a prior art cartridge.

FIG. 23 shows one embodiment of the cartridge 60. The cartridge 60 is shaped so that it fits into the medicine chamber 45 and can spin freely therein. It is provided with an opening 65 so that the nebulizing stem 55 can be introduced into the cartridge 60 and access the medicament contained in the cartridge 60 through the opening 65. FIG. 23 shows the cartridge 60 for use with the nebulizer 25. As shown in FIG. 23, the cartridge 60 is generally a three-dimensional octagonal shape filled with a medicament. In one embodiment, the cartridge 60 is formed from plastic, preferably biodegradable. As shown in FIG. 24, the prior art cartridges for containing medicament are generally of three-dimensional shape and have a twist opening located at the proximal or distal end of the cartridge. Rather, the improved cartridges 60 may have a twist opening located on the surface of one of the octagons forming the top and bottom of the cartridge. In another embodiment, the cartridge 60 may have a weakened perforated area on the surface of the cartridge 60 through which the nebulizing stem 55 can be easily introduced. As shown in FIG. 23, the novel shape of the cartridge 60 allows for it to fit within the medicine chamber 45 of the nebulizer 25. The cartridge 60 then sits in the medicine chamber 45 and is capable of spinning while seated in the medicine chamber 45. The nebulizing stem 55 can be introduced into the cartridge 60 at the cartridge opening 65 caused by the removal of the twist-off cap 70. Using the cartridge 60 in the nebulizer 25 facilitates the delivery of proper dosage by providing a cartridge 60 pre-packaged with a proper dosage amount; the dosage being variable by medicament, ailment, patient and the like. Also, the cartridge 60 facilitates the use of the nebulizer 25 with a variety of various medicaments. Since the cartridge 60 is placed into the medicine chamber 45, the medicine chamber 45 itself does not fill with a variety of different medications. This eases the cleaning process of the medicine chamber 45. It also prevents the intermixing of different medicaments in the medicine chamber 45. For example, by using the cartridge 60, the same nebulizer 25 can be used to deliver two different medications at different times to different patients with more certainty that the different medications would not intermix in the medicine chamber 45. Without the use of the cartridge 60, when the medicine chamber 45 is filled first with one medicament and later with another medicament for delivery via use of the nebulizer 25, if the medicine chamber 45 is not properly and thoroughly cleaned, the two different medicaments inserted into the medicine chamber 45 may intermix, causing possibly hazardous or toxic situations. The use of the cartridge 60 greatly reduces the chances of intermixing of two medicaments and facilitates or increases the ease of cleaning of the medicine chamber 45.

In other embodiments, rather than using the cartridge 60, the nebulizer 25 is capable of accepting a multi-dose cartridge 75. In use, the multi-dose cartridge 75 may be filled with, for example, a week's supply of a particular medicament. The nebulizer 25 would then be provided with a dosing system so that each time medicament is dispensed from the multi-dose cartridge 75, it is dispensed in a dose-specific amount. In other aspects of this embodiment, the multi-dose cartridge 75 may be filled with enough medicament for a daily dose, bi-weekly dose, a weekly dose, a bi-monthly dose, and other variety of dosage amounts.

In another aspect of the embodiment of the cartridge 60, it is envisioned that the cartridge 60 may be an octagonal shape, a circular shape, an oval shape, and any other variety of shape which would be cooperative with the medicine chamber 45.

As shown in FIGS. 11-15, the nebulizer 25 includes a tube 80 for delivering compressed air in cooperation with nebulized particles from the medicine chamber 45. The tube 80 may also deliver any other gas or combination of gases. The nebulizer 25 also includes a particle dispersion chamber 85. The particle dispersion chamber 85 is associated with a nasal adapter 10. As the nebulized particles travel from the medicine chamber 45 through the compressed air tubing 80, they reach the particle dispersion chamber 85. As the particles are passed through the particle dispersion chamber 85, they are swirled into a vortex and emerge from the chamber 85 while still in the vortex into the nasal cavity and the paranasal sinuses. In this process, the individual particles are themselves caused to spin and are caught up in the vortex. The particles advantageously enter the nasal cavity at many angles. The particles also bounce or ricochet within the nasal cavity allowing the particles to reach previously impossible areas.

Figure 11:
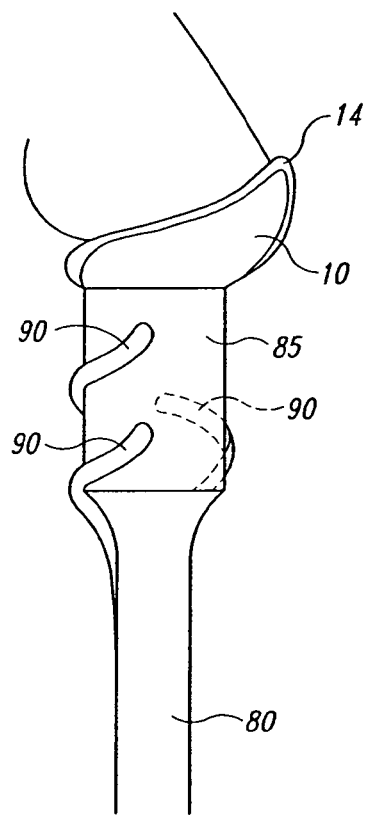
FIG. 11 shows one embodiment of the particle dispersion chamber, the tubing, and the nasal adapter.

In one embodiment of the particle dispersion chamber 85 as shown in FIG. 11, as the particles exit the compressed air tubing 80 and enter the particle dispersion chamber 85, they come into contact with a variety of air outputs 90. The air outputs 90 may be positioned either randomly along the particle dispersion chamber 85 or in a set array. The air outputs 90 are, for example, a plurality of air jets which spurt, blow or vent, or the like, into the particle dispersion chamber 85 and cause the nebulized particles within the chamber 85 to randomly move in a vortex. This random movement of the particles in a vortex continues while the particles travel through the nasal adapter 10, eventually into the nose and into the nasal cavity and paranasal sinuses.

Figure 12:
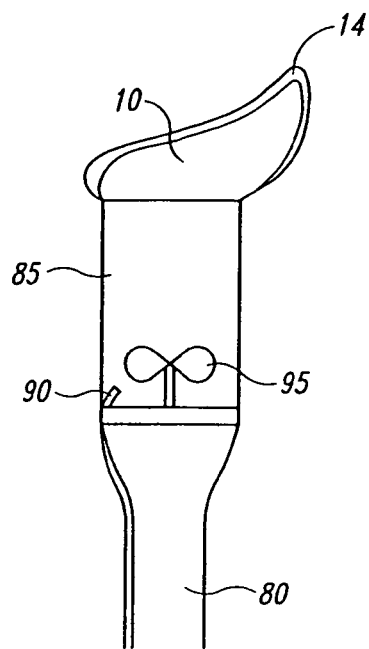
FIG. 12 shows a further embodiment of the nasal adapter, particle dispersion chamber, and tubing.

In a further embodiment, as shown in FIG. 12, the nebulized particles once again travel through the tubing 80 and into the particle dispersion chamber 85. In the embodiment shown in FIG. 12, the particle dispersion chamber 85 contains at least an air output 90 and a dispersion blade 95. The dispersion blade 95 may have solid blades or blades made of netting or openings. Movement of the dispersion blade 95 is created through spurts or jets of air exiting from the air output 90. Alternatively, movement of the dispersion blade 95 can be created using a motor. A variety of other equivalent movement mechanisms varying from magnetic to a wind-up spring can be used to create movement of the dispersion blade 95. As the dispersion blade 95 rotates within the particle dispersion chamber 85, the nebulized particles exiting from the tubing 80 into the dispersion chamber 85 come into contact with the movement from the dispersion blades 95 and are caused to randomly move within the dispersion chamber 85 in a vortex. As the particles exit the particle dispersion chamber 85 and the nasal adapter 10, they enter the nasal cavity and paranasal sinuses and the paranasal sinuses still exhibiting random motion in the vortex.

Figure 13:
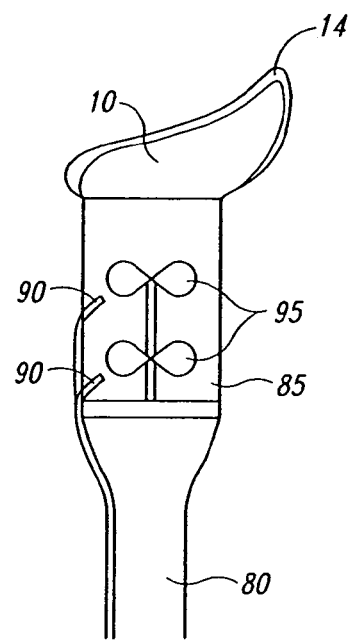
FIG. 13 shows yet another embodiment of the nasal adapter, particle dispersion chamber, and tubing.

As shown in FIG. 13, a plurality of dispersion blades 95 and outlets 90 may be located in the particle dispersion chamber 85. This plurality of blades 95 may rotate all clockwise, all counterclockwise, or in opposite directions from one another around an axis of rotation. The dispersion blades 95 create motion of the nebulized particles in a vortex within the particle dispersion chamber 85. The nebulized particles exit the particle dispersion chamber 85 and nasal adapter 10 still in a vortex and enter into the nasal cavity and paranasal sinuses.

Figure 14A:
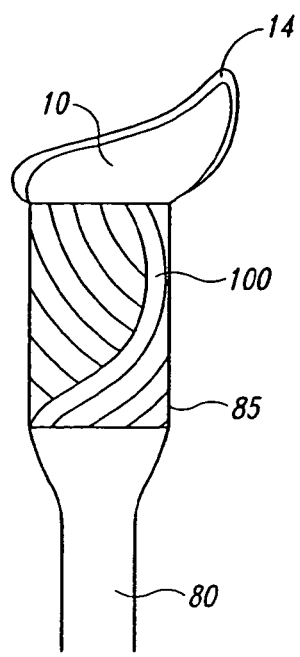
FIG. 14a shows another embodiment of the nasal adapter, particle dispersion chamber, and tubing.
Figure 14B:
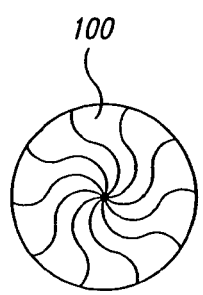
FIG. 14b shows a bottom view of one embodiment of the baffle.

In the embodiment shown in FIG. 14, the nebulized particles exit the tubing 80 and come into contact with a baffle 100 located in the particle dispersion chamber 85. The baffle 100 is shaped so as to create movement of the particles while in a vortex. As shown in FIG. 14, the baffle 100 is generally serpentine shape. Although in FIG. 14 the baffle 100 is shown in a generally serpentine or helix shape, it is understood that any baffle 100 shape which would create motion of the nebulized particles in a vortex as they exit the dispersion chamber 85 is equivalent. For example, a helixical shaped baffle 100 may create motion of the particles in a vortex.

Figure 15:
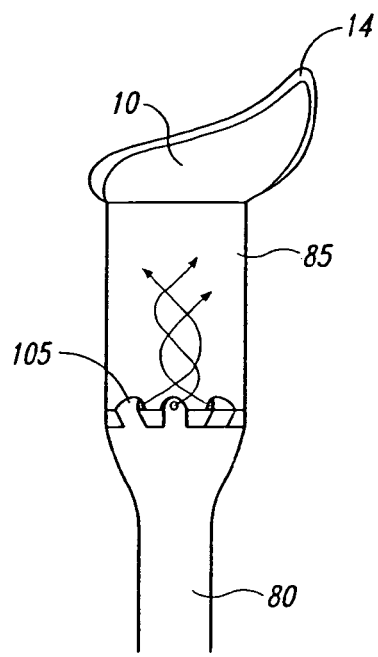
FIG. 15 shows yet another embodiment of a nasal adapter, particle dispersion chamber, and tubing.

The embodiment shown in FIG. 15 includes a particle dispersion chamber 85 having a plurality of directional output nozzles 105. The directional output nozzles 105 spray, spurt, vent, jet, or the like, air into the particle dispersion chamber 85 so as to create a vortex of nebulized particles. The particles remain in a vortex and continue to travel in a manner even when exiting the particle dispersion chamber 85 and introduced into the nasal cavity and paranasal sinuses.

The particle dispersion chambers 85 described herein can also be adopted for use with current pressurized canister inhalers, dry powder inhalers, inhaler and other mechanisms for which medicine is breathed through the nose, mouth, or both including inhaling and exhaling through the same orifice or alternating between the orifices. A small pump 35, either hand-primed, electric, or battery powered or otherwise, is attached to a housing and is prepared to be actuated. Tubing 80 which leads to air ports 90 lead from the pump 35 to a particle dispersion chamber 85 placed over the exit off the actuator 120. The pump fires when the unit is actuated and creates a vortex of the particles prior to the medicament entering the nostril where it can be swirled into the nasal cavity. The pump 35 can be fired by hand and timed with the breathing process of the user with such versions as a dry powder inhaler which uses the user's breathing to release the powder into the system.

Figure 16:
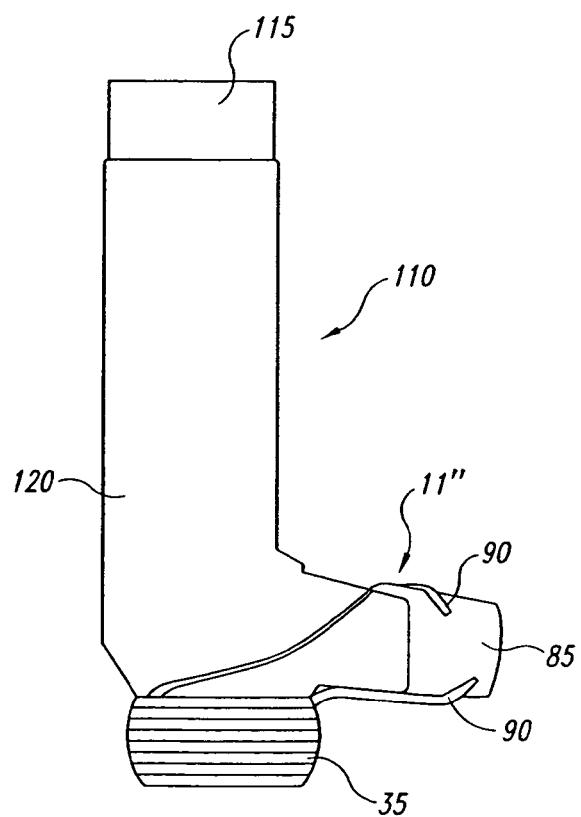
FIG. 16 shows an inhaler with one embodiment of a particle dispersion chamber.

FIG. 16 shows an inhaler 110 having a mouthpiece 11, a pump 35, a pressurized canister 115 of medicine, and an actuator 120. To the inhaler 110 can be attached at the mouthpiece 11 a particle dispersion chamber 85. The embodiment of FIG. 16 shows an inhaler 110 having a particle dispersion chamber 85 with a plurality of air outports 90, although other embodiments of the particle dispersion chamber 85 can be associated with the inhaler 110.

Figure 17:
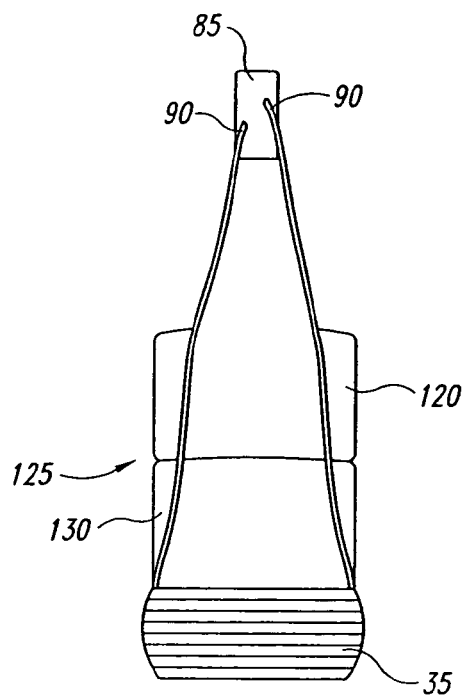
FIG. 17 shows a nasal spray with one embodiment of a particle dispersion chamber.

FIG. 17 shows a nasal spray 125 having a pump 35, a particle dispersion chamber 85 with a plurality of air ports 90, a nasal spray actuator 120, and a nasal spray medicine container 130. The embodiment of FIG. 17 shows a nasal spray inhaler 125 having a particle dispersion chamber 85 with a plurality of air outports 90, although other embodiments of the particle dispersion chamber 85 can be associated with the nasal spray inhaler 125.

Figure 18:
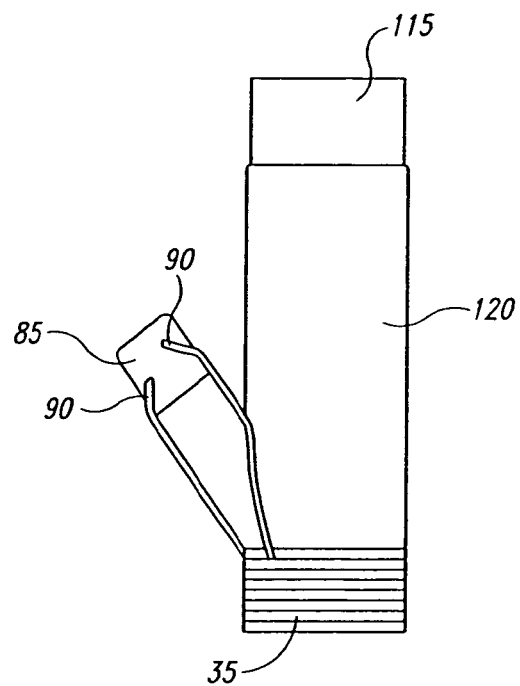
FIG. 18 shows a nasal inhaler with one embodiment of a particle dispersion chamber.

FIG. 18 shows an inhaler 110 having a pump 35, a pressurized canister 115 of medicine, and an actuator 120. To the inhaler 110 can be attached a particle dispersion chamber 85. The embodiment of FIG. 18 shows an inhaler 110 having a particle dispersion chamber 85 with a plurality of air outports 90, although other embodiments of the particle dispersion chamber 85 can be associated with the inhaler 110.

Figure 19:
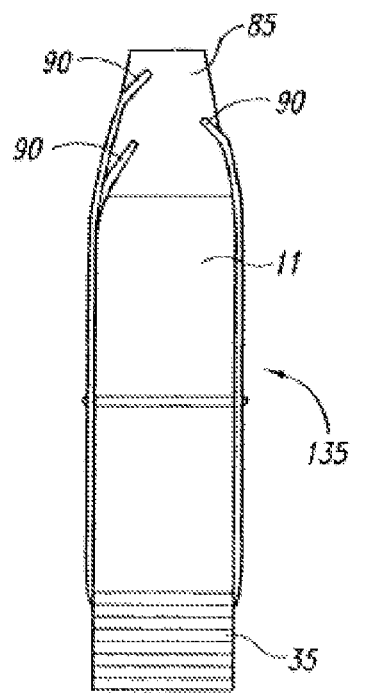
FIG. 19 shows a dry powder spinhaler with one embodiment of a particle dispersion chamber.

FIG. 19 shows a dry powder inhaler 135 having a mouthpiece 11 and a pump 35. To the dry powder inhaler 135 can be attached a particle dispersion chamber 85. The embodiment of FIG. 19 shows the dry powder inhaler 135 having a particle dispersion chamber 85 with a plurality of air outports 90, although other embodiments of the particle dispersion chamber 85 can be associated with the dry powder inhaler 135.

Figure 20:
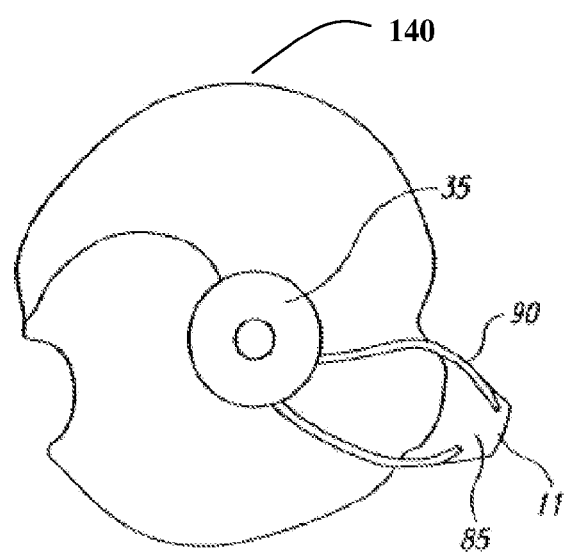
FIG. 20 shows a dry powder inhaler with one embodiment of a particle dispersion chamber.

FIG. 20 shows a dry powder inhaler 140 having a mouthpiece 11 and a pump 35. To the dry powder inhaler 140 can be attached a particle dispersion chamber 85. The embodiment of FIG. 20 shows the dry powder inhaler 140 having a particle dispersion chamber 85 with a plurality of air outports 90, although other embodiments of the particle dispersion chamber 85 can be associated with the dry powder inhaler 135. In a pulmonary application using a dry powder inhaler 140, the particle dispersion chamber 85 serves to break down the particles further reducing clumping and increasing the amount that reaches the lungs. In pulmonary inhaler versions, the medicament is greater dispersed and increases the opportunities for it to get into the throat without been blocked by the tongue.

In an embodiment, there are two air outputs 90, or jets, and a third jet is used to spin the particles prior to them entering the chamber 45. This is designed to get the individual particles spinning prior to being put into the vortex in the chamber 45. This will allow the particles to get better "bounce" in the nasal cavity and deeper penetration and larger coverage area into the nasal cavity and the sinuses.

This will be done for specific medicaments that could benefit from this action and will be turned off for medicaments that would not benefit from it.

In another embodiment, prior to the nebulized particles entering the dispersion chamber 85, they will pass through a charge station where they will gain a negative or positive charge which causes the particles to repel each other and does not allow them to recombine into larger particles. This will cause the particles to repel each other in the chamber 85, the nasal cavity, and sinuses allowing for deeper penetration and larger coverage area. This will be done for specific medicaments that could benefit from this action and will be turned off for medicaments that would not benefit from it.

In one manner of operation, a cartridge 60 containing a medicament or the medicament itself is placed into the medicine chamber 45 of the nebulizer 25 shown in FIG. 1. The nasal adapter 10 is fitted over the nose of the user and the nebulizer 25 is activated. The user breathes using the BT. More particularly in operation:

1. In FIG. 1, the lid 50 is lifted to the medicine chamber 45 and the prescribed dosage of medicine is poured in. The lid 50 is then closed.
2. The nasal adapter 10 is lifted from its compartment 2, shown in FIG. 1, in the topside of the nebulizer 25 to the required height.
3. As shown in FIG. 11, the nasal adapter 10 is placed over the nose and pressed into place to seal in the nebulized particles.
4. As shown in FIG. 3, the timer 4 is set to the required time for the drug being used.
5. As shown in FIG. 3, the start button 6 is activated, for example, by being depressed.
6. The user breathes using the BT, but inhaling and exhaling out the mouth as needed to maintain oxygen levels.
7. When the timer 4 stops the nebulizer 25, if it is being used for a single dose treatment, the nasal adapter 10 is replaced in its compartment 2 and the medicine chamber 45 is cleaned. The nebulizer 25 should be allowed to dry fully before reusing. If using for a multiple dose treatment, it should be cleaned after each dosage is complete.

The nebulizer 25 disclosed herein is capable of delivering nebulized particles far into the nasal cavity and the paranasal sinuses. In another method of operation, the user uses the nebulizer 25 in conjunction with a Controlled Particle Dispersion Breathing Technique (BT). The BT provides for the nebulized particles to reach deeply into the nasal cavity and paranasal sinuses. The BT includes placing the nasal adapter 10 of the nebulizer 25 over the nose of the patient and activating the nebulizer 25. As nebulized particles begin to flow out of the particle dispersion chamber 85, the user should take approximately one to five quick breaths, preferably two to four quick breaths, and even more preferably three breaths, through the user's nose. The breath(s) should be held for approximately one to five seconds and more preferably for three seconds. Using the back of the throat, the user should then create pressure in their sinuses such as when relieving pressure due to a change in altitude when traveling in a car or plane. This allows the medicine to remain in the nasal cavity and aids in delivery of the medicine to the sinuses. The breathing, breath holding, and pressure creation should be performed from two to four times in succession and preferably for two times in succession. After the breathing, breath holding, and pressure creation are performed in succession, the user should follow with one to four slow, long deep breaths through the nose. Preferably, the user should follow with three long, slow, deep breaths through the nose. More preferably, the user should follow with two long, slow deep breaths through the nose. Most preferably, the user should follow with one long, slow, deep breath through the nose. The above discussed breathing, breath holding, pressure creation, and slow, long deep breaths are then repeated until the treatment is complete. It is advised that when dealing with severe cases of sinus congestion, the user should be instructed to breathe through the mouth as needed to maintain necessary oxygen intake. Although the BT involves breathing in through the nose, it is understood that infants, children, the elderly and others with serious breathing problems may perform the BT through the mouth or through cooperatively the mouth and nose.

The nebulizer 25 disclosed herein is capable of delivering nebulized particles far into the ethmoid, maxillary and sphenoid sinus. The sphenoid sinus is located furthest from the nasal cavity. The ethmoid, maxillary and sphenoid sinuses have not been penetrated in the past through any other prior art technology. The delivery of medicament to the ethmoid, maxillary and sphenoid sinuses has been shown through sinus ventilation studies.

Example 1

A 21-year-old female subject was provided with the nebulizer 25 and was instructed to perform the Controlled Particle Dispersion Breathing Technique (BT). A TC-DTPA aerosol radiopharmaceutical was provided in the nebulizer 25 in a dose of 10 mci. After performance of the BT, a technesium imaging test was performed on the nasal sinuses of the subject. The technesium imaging test was performed at Swedish Medical Center in Seattle, Wash. The technesium imaging test allows for identification of nebulized particles in the ethmoid and sphenoid sinuses. The findings of the technesium imaging tests were of tracer activity in the ethmoid and sphenoid sinuses bilaterally. There was no activity in the maxillary or frontal sinuses. Communication between the nasal airway and ethmoidal and sphenoid sinuses was documented.

Example 2

A 25-year-old male subject was provided with the nebulizer 25 and instructed to perform the Controlled Particle Dispersion Breathing Technique (BT). The nebulizer 25 was provided with TC-DTPA aerosol at a dose of 15 mci. The technesium imaging test was performed at Swedish Medical Center in Seattle, Wash. The technesium imaging test allows for identification of nebulized particles in the ethmoid and sphenoid sinuses. The findings of the technesium imaging study were that proton activity was greater in the ethmoid, maxillary and sphenoid sinuses bilaterally greater right than left. There was no tracer activity in the frontal sinuses. The aerosol was delivered via a nasal mask communicated with the ethmoid and sphenoid sinuses bilaterally but not with the frontal sinuses.

Figure 21:
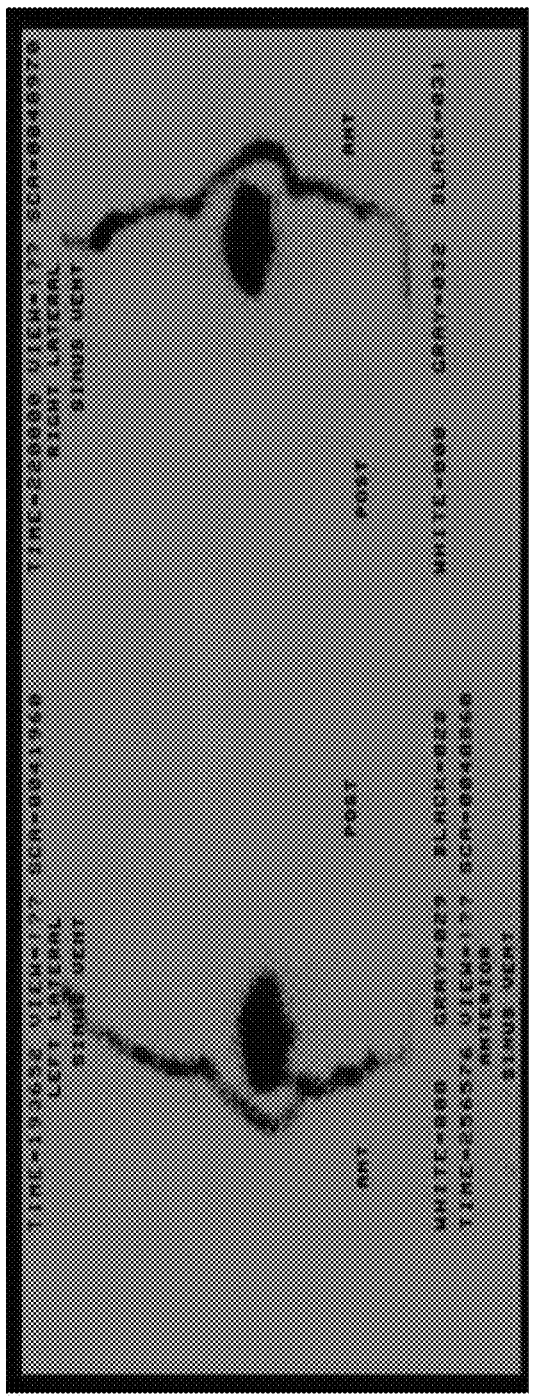
FIG. 21 shows the results of a sinus ventilation study using a prior art drug delivery apparatus.
Figure 22:
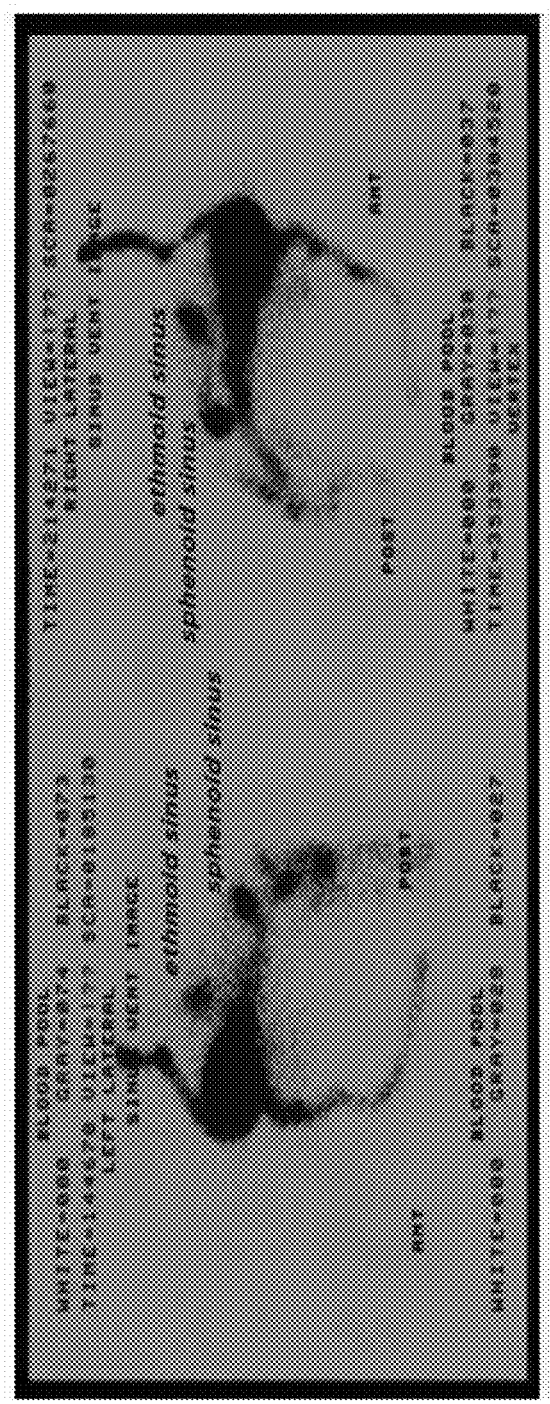
FIG. 22 shows the results of the sinus ventilation study using an embodiment of the nebulizer with a particle dispersion chamber for delivery of medicament to the sinus cavity.

A representative sinus-bent image for the subjects in Examples 1 and 2 is provided in FIG. 22. FIG. 22 shows delivery to the ethmoid, maxillary and sphenoid sinuses via the nebulizer 25. Prior art FIG. 21 shows no penetration into any of the paranasal sinuses and far less penetration of the nasal cavity. The exposed area in FIG. 22 using the nebulizer 25 is significantly larger with more absorption area. Most notably, the drug penetrated the ethmoid and sphenoid sinuses. The drug delivered through the nebulizer 25 and via the BT did provide a path to the throat.

All of these features have been built into the device for use as a nasal nebulizer for the treatment of chronic sinusitis, allergic rhinitis, colds and flu, pain relief and for any developments in which introduction of drugs via the nasal passages will be aided. In one potential embodiment the nebulizer 25 will be used to deliver various medicaments with a narrow range of particle sizes.

While the preferred embodiment of the invention has been illustrated and described, it will be appreciated that various changes can be made therein without departing from the spirit and scope of the invention.

The invention claimed is:

1. A particle dispersion chamber comprising:
    a housing having an external surface, a particle input end, and outputs opening, and an internal channel between the particle input end and the output opening, the channel generally defining a channel axis and a forward direction toward the output opening, the internal channel having a substantially continuous cross-sectional area from the particle input end of the housing to, and including the output opening; and
    a plurality of directional fluid outputs configured within the housing to direct output at an acute forward angle with respect to the channel axis and output opening, wherein the fluid outputs, when fluid flows therefrom, are operative to impart a vortical flow to aerosolized particles exiting the output opening.

2. A method of delivering a medicament to the nasal cavity and paranasal sinuses of a subject, comprising:
    providing the particle dispersion chamber of claim 1; and
    delivering an aerosolized medicament in a vortical flow to the nasal cavity and paranasal sinuses of a subject.

3. The method of claim 2, wherein the medicament is at least one of a treatment for conditions consisting of sinusitis, allergies, rhinitis, migraine headache, influenza, and the common cold.

4. The particle dispersal chamber of claim 1, wherein the air outputs are positioned randomly along within the housing of the particle dispersion chamber.

5. The particle dispersion chamber of claim 1, wherein the air output are positioned in a set array within the housing of the particle dispersion chamber.

6. The particle dispersion chamber of claim 1 wherein the air outputs are jets.

7. The particle dispersion chamber of claim 1 further comprising a dispersion blade located within the internal channel.

8. The particle dispersion chamber of claim 7 wherein the dispersion blade is solid.

9. The particle dispersion chamber of claim 7 wherein the dispersion blade is netting.

10. The particle dispersion chamber of claim 1 further comprising a baffle located within the internal channel.

11. The particle dispersion chamber of claim 10 wherein the baffle is helixical shaped.

12. The particle dispersion chamber of claim 1 further comprising: an inhaler having a mouthpiece, the mouthpiece associated with the particle dispersion chamber.

13. The particle dispersion chamber of claim 1 further comprising: a nasal spray inhaler having an actuator, the actuator associated with the particle dispersion chamber.

14. The particle dispersion chamber of claim 1, further comprising a nasal adapter.

15. The particle dispersion chamber of claim 1 further comprising: a dry powder inhaler having an mouthpiece, the mouthpiece associated with the particle dispersion chamber.

16. A method of delivering aerosolized particles into a nasal cavity of a subject, comprising:
    providing a particle delivery chamber, comprising a housing having an external surface, a particle input end, and output opening, an internal channel between the particle input end and the output opening, the internal channel generally defining a channel axis and a forward direction toward the output opening, the housing additionally having at least one directed fluid output channel configured to direct fluid output at an acute forward angle with respect to the channel axis and output opening;
    introducing aerosolized particles into the internal channel;
    imparting, using fluid flow from the at least one directed fluid output channel, a vortical flow pattern to said particles exiting the output opening of the internal channel; and
    delivering the vortically flowing particles into a nasal cavity of the subject, wherein a method of delivering aerosolized particles to the nasal cavity is afforded.

17. The method of claim 16, comprising delivering the aerosolized particles to an ethmoid, maxillary, or sphenoid paranasal sinus.

18. The method of claim 16, comprising delivery of particles sizes ranging from about 2 to about 50 microns, or from about 2 to about 15 microns.

19. The particle dispersion chamber of claim 14, wherein the nasal adapter has a lip.

20. The particle dispersion chamber of claim 14, wherein the nasal adapter has a width of about 1½ inches across a bridge of the nasal adapter and a length of about 1½ inches.

21. The particle dispersion chamber of claim 19, wherein the lip is about ⅛ inch long and capable of forming a seal.

22. The particle dispersion chamber of claim 14, wherein the nasal adapter has a plurality of exhaust vents.

* * * * *